US006515166B1

(12) United States Patent
Grundke et al.

(10) Patent No.: US 6,515,166 B1
(45) Date of Patent: Feb. 4, 2003

(54) VINYL ESTERS WITH HIGH CROSS-LINKAGE DENSITY

(75) Inventors: Ulrich Grundke, Duisburg (DE); Klaus-Peter Liebetanz, Duisburg (DE); Volker Kalla, Duisburg (DE)

(73) Assignee: Bakelite AG (DE)

( * ) Notice: Subject to any disclaimer, the term of this patent is extended or adjusted under 35 U.S.C. 154(b) by 0 days.

(21) Appl. No.: 09/694,442

(22) Filed: Oct. 23, 2000

(30) Foreign Application Priority Data

Nov. 25, 1999 (DE) .......................... 199 56 779

(51) Int. Cl.$^7$ .......................... C07C 67/26; C08G 85/00
(52) U.S. Cl. .......................... 560/209; 526/72
(58) Field of Search .................. 560/209, 129

(56) References Cited

U.S. PATENT DOCUMENTS 3,676,398 A * 7/1972 D'Alelio ................ 260/47

FOREIGN PATENT DOCUMENTS

| CA | 2132106 | * | 9/1998 |
| DE | 4209248 | | 9/1993 |

OTHER PUBLICATIONS

XP–002159028, 2 pages, 10/96.
XP–002159027, 1 page, Mar. 16, 1990.
XP–002159030, 1 page, Sep. 30, 1977.

* cited by examiner

Primary Examiner—Mark L Berch
Assistant Examiner—Zachary C. Tucker
(74) Attorney, Agent, or Firm—Bierman, Muserlian and Lucas

(57) ABSTRACT

A vinyl ester produced by reacting at least one epoxide compound with at least on carboxylic anhydride, containing ethylenically unsaturated groups, the epoxide groups being substantially substituted by two vinyl ester groups.

9 Claims, No Drawings

VINYL ESTERS WITH HIGH CROSS-LINKAGE DENSITY

STATE OF THE ART

Vinyl esters of epoxides and unsaturated acid anhydrides are used as photo-curing prepolymers and as surface coating resins having good electrical properties, high adhesion on most substrates and good chemical resistance. However, there is a need for highly reactive vinyl esters having in addition to said good properties, also good temperature stability and better chemical resistance.

Reaction products of epoxide compounds with unsaturated acid anhydrides and/or carboxylic acids are known per se. However, in these products, the epoxide groups are only partially esterified with the epoxide groups being substituted by β-hydroxy vinyl ester groups. JP-A-02077417 discloses, for example, coating agents for metal containers, which comprise a binding agent which is converted by conversion of 90–99.95% by weight of an aromatic epoxy resin with 0.05–10% by weight of acrylic and/or methacrylic anhydride.

DE-A-42 09 248 describes graft polymers, in which in a first step, epoxy resins are heated with small amounts of acrylic and/or methacrylic anhydride and these products are then reacted with other ethylenically unsaturated compounds. From JP-A-08259663 are known radiation-curable vinyl esters, in which in a first reaction step, epoxy resins are reacted with 0.1–0.8 mole of acrylic and/or methacrylic anhydride and with 0.2–0.9 mole of unsaturated carboxylic acid per mole of epoxide group. Then, conversion of these reaction products or the β-hydroxy groups of these vinyl esters with multivalent acid anhydrides is effected.

OBJECTS OF THE INVENTION

It is an object of the invention to provide vinyl esters with good temperature stability and improved chemical resistance and a process for their preparation.

It is another object of the invention to provide improved surface coating resins and photo-curing prepolymers.

These and other objects and advantages of the invention will become obvious from the following detailed description.

THE INVENTION

The vinyl esters of the invention are produced by reacting at least one epoxide compound with at least one carboxylic acid anhydride containing ethylenically unsaturated groups, the epoxide groups being substantially substituted by two vinyl ester groups. It has been found that vinyl esters substantially free of β-hydroxy groups are obtained if the epoxide compounds are reacted with stoichiometric amounts of ethylenically unsaturated carboxylic acid anhydrides.

For example, in the reaction of bisphenol A or bisphenol F diglycidyl ethers with acrylic acid or methacrylic acid in stoichiometric quantities with respect to the epoxide groups, vinyl esters are obtained with an equivalent weight of 250 to 300 g of resin/double bonds. In the corresponding reaction with acrylic acid anhydride or methacrylic acid anhydride, vinyl esters are formed with an equivalent weight of 170 to 200 g of resin/double bonds.

In the products obtained by the invention, the epoxide groups are substantially substituted by two vinyl ester groups. These vinyl esters exhibit the same good property profile as the known vinyl esters, but yield an increased cross-linkage density after curing which leads to higher resistance to chemicals and better temperature stability. The vinyl esters with high cross-linkage density of the invention surprisingly have a markedly lower viscosity than vinyl esters comprising simple β-hydroxy groups. They are useful for surface coating, resins, photo-curing components in coating agents and as binding agents in chemical reaction resin materials, particuarly for chemical anchoring agents.

For example, in a varnish formulation at identical monomer fraction, there is obtained a lower processing viscosity, which means, to attain the same final viscosity, the fraction of monomers or solvents can be decreased. This leads yet again to a further increase of the resistance to chemicals and better temperature stability. A further surprising advantage comprises that the vinyl esters of the invention with high cross-linkage density, nevertheless, have an improved storage life. They can be stored at ambient temperature for up to 52 weeks without a substantial increase of their viscosity being observed.

Examples of epoxide compounds for the production of the vinyl esters of the invention are all monomeric or oligomeric compounds, glycidyl ethers, glycidyl esters or N-glycidyl compounds with one or more epoxide groups, known per se. Preferred are epoxide compounds with two and more epoxide groups in the molecule, particularly diglycidyl ethers of bisphenols as well as glycidyl ethers of novolaks based on phenol, cresol or bisphenols.

In principal, as ethylenically unsaturated carboxylic acid anhydrides can be used all carboxylic acid anhydrides of monocarboxylic acids, which have one or more ethylenically unsaturated groups. The preferred anhydrides are acrylic acid anhydride and methacrylic acid anhydride.

The reaction of the epoxide compounds with the ethylenically unsaturated acid anhydrides takes place in a manner known per se by combining the components in corresponding quantities, using a solvent if appropriate, a catalyst known per se and a stabilizing agent acting as a radical interceptor, such as, hydroquinone, p-benzoquinone, methylhydroquinone, catechol and the like.

The catalyst is selected from the groups of metal salts, known per se, such as dibutyl tin dilaurate, tin octoate, phosphorus compounds, such as triphenyl phosphine or ethyl triphenyl phosphonium bromide, tert. amines, such as dimethylaminopyridine or benzyl dimethylamine or quaternary ammonium compounds, such as tetraethyl ammonium bromide. The particular reaction mixture is then heated for several hours at temperatures in the range of 80 to 120° C. In this reaction oxygen, or a gas comprising oxygen, is preferably conducted through the reaction mixture to prevent polymerization.

In the conversion of hydroxyl group-free epoxide compounds with the ethylenically unsaturated acid anhydrides, a small amount of a carboxylic acid is preferably added to accelerate the start of the esterification reaction. Preferred are ethylenically unsaturated carboxylic acids, in particular acrylic acid and/or methacrylic acid. With increasing amounts of added carboxylic acid, on the one hand, the start of the esterification reaction is accelerated, on the other hand, however, the content of vinyl ester groups is decreased. Balancing these two criteria against one another, therefore the amount of the added carboxylic acid is selected so that it is within the range of up to 0.1 mole, preferably up to 0.05 mole, more preferably up to 0.01 mole per mole of epoxide groups. The amounts of ethylenically unsaturated acid anhydrides used in this case must be correspondingly reduced so that per mole of epoxide group are used 0.9 to 1 mole of ethylenically unsaturated acid anhydride and 0.1 to 0 mole of carboxylic acid, preferably 0.95 to 1 mole of ethylenically unsaturated acid anhydride and 0.05 to 0 mole of carboxylic acid, and, most preferably 0.99 to 1 mole of ethylenically unsaturated acid anhydride and 0.01 to 0 mole of carboxylic acid.

If the epoxide compounds used comprise hydroxyl groups, such as is the case with epoxy resins which are produced by reaction of bisphenol with epichlorhydrin and subsequent advancement reaction, omission of a starter acid is preferred.

The processing of the reaction mixture also takes place in a manner known per se by carefully distilling off the solvent which optionally had been used, and, if appropriate, by adding a further stabilizing agent. As a rule, liquid products are obtained which are curable by radiation, heat or by means of catalysts. Due to their properties, they are preferably used as surface-coating resins, as photo-curing components in coating agents as well as binding agents or binding agent component in chemical resin materials, in particular such for the production of chemical anchoring means.

In the following examples, there are described several preferred embodiments to illustrate the invention. However, it is to be understood that the invention is not intended to be limited to the specific embodiments.

EXAMPLE 1

Into a reactor provided with a stirrer, thermometer, gas inlet tube and addition device, there was placed 368 g (1 mole) of bisphenol A diglycidyl ether, 4.0 g of triphenyl phosphine and 0.5 g of hydroquinone monomethyl ether, and the mixture was heated to approximately 90° C. While stirring the mixture and continuously introducing gas, 17.2 g (0.2 mole) of methacrylic acid were added over 15 minutes. Immediately following, under the same conditions, 277.2 g (1.8 mole) of methacrylic anhydride were added over an additional period of 2 hours. The reaction mixture was maintained at 90° C while it was stirred and air was introduced until it had an acid number of <5 mg of KOH/g. A vinyl ester resin was formed with a viscosity at 40° C. of 9,000 mPas and a double bond density of 175 g of resin per double bond. After storage at 100° C., the following increase in viscosity was measured:

| 7 d 100° C. | 118% |
|---|---|
| 14 d 100° C. | 138% |
| 28 d 100° | 149% |

Example 2 (Comparison Example)

Into a reactor provided with a stirrer, thermometer, gas inlet tube and addition device, there were placed 368 g (1 mole) of bisphenol A diglycidyl ether, 4.0 g of triphenyl phosphine and 0.5 g of hydroquinone monomethyl ether, and the mixture was heated to approximately 90° C. While stirring the mixture and continuously introducing air, 72 g (2 mole) of methacrylic acid were added over a period of 2 hours. The reaction mixture was maintained at 90° C. while it was stirred and air was introduced, until it had attained the acid number <5 mg of KOH/g. A vinyl ester was formed with a viscosity of 40° C. approximately 47,000 mPas and a double bond density of 270 g of resin per double bond.

After storage at 100° C., the following increase in viscosity was measured:

| 7 d 100° C. | 154% |
|---|---|
| 14 d 100° C. | 200% |
| 28 d 100° C. | gel formation |

Example 3

The two vinyl esters from Examples 1 and 2 were diluted with trimethylol propane trimethacrylate (TRIM):

50 GT vinyl ester from Example 2
50 GT TRIM
Viscosity of the mixture at 25° C.:2,100 mPas
50 GT vinyl ester from Example 1
50 GT TRIM
Viscosity of the mixture at 25° C.:950 mPas
60 GT vinyl ester from Example 3
40 GT TRIM
Viscosity of the mixture at 25° C.:2,000 mPas To verify the resistance to chemicals, the mixtures a to c were set with Co-amine accelerator and tert.butyl peroxibenzoate to a gelling time of 30 minutes. With the mixtures a', b' and c', thus produced sample bodies were produced having the dimensions 50×50×3 mm. After curing (7 days at ambient temperature), the sample bodies a', b' and c' were each stored for 50 and 100 hours at 100° C. in 10% aqueous sodium hydroxide, subsequently rinsed, dried with wood pulp paper and subsequently weighed. The following increases in weight were found:

| | Sample body from Mixture: | | |
|---|---|---|---|
| Weight increase (%) | a' | b' | c' |
| after 50 hours | 2.6 | 1.2 | 1.05 |
| after 100 hours | 3.2 | 1.4 | 1.1 |

Various modifications of vinyl esters and the compositions may be made without departing from the spirit or scope thereof and it is to be understood that the invention is intended to be limited only as defined in the appended claims.

What we claim is:

1. A vinyl ester with an equivalent weight of 170 to 200 produced by reacting at least one epoxide compound with first 0.001 to 0.1 mole of a carboxylic acid per mole of epoxide group and then with 0.9 to 1 mole of at least one carboxylic acid anhydride containing ethylenically unsaturated groups per mole of epoxide group, the epoxide groups in the epoxide compound before reaction being substituted by two vinyl ester groups.

2. A vinyl ester of claim 1 wherein 0.95 to 1 mole of unsaturated acid anhydride and 0 to 0.05 mole of carboxylic acid per mole of epoxide group.

3. A vinyl ester of claim 1 wherein there are 0.99 to 1 mole of unsaturated acid anhydride and 0 to 0.01 mole of carboxylic acid per mole of epoxide group are selected from the vinyl ester.

4. A vinyl ester of claim 1 wherein the unsaturated acid anhydride is at least one member of the group consisting of acrylic acid anhydride and methacrylic acid anhydride.

5. A vinyl ester of claim 1 wherein the carboxylic acid is at least one member of the group consisting of acrylic acid and methacrylic acid.

6. In a reaction resin material for production of chemical anchoring means, the improvement comprising a vinyl ester of claim 1 as a binding agent for the resin material.

7. In a chemical reaction resin material, the improvement comprising a vinyl ester of claim 1 as a binding agent for the said resin material.

8. In a coating agent to be photo cured, the improvement comprising a vinyl ester of claim 1 as a photo-curing component for the catalyst agent.

9. In a surface coating agent, the improvement comprising a vinyl ester of claim 1 as a component of the coating agent.

* * * * *